United States Patent [19]

Micko

[11] 4,305,724
[45] Dec. 15, 1981

[54] COMBUSTIBLE GAS DETECTION SYSTEM

[75] Inventor: Eric S. Micko, Los Altos Hills, Calif.

[73] Assignee: Delphian Partners, Sunnyvale, Calif.

[21] Appl. No.: 175,026

[22] Filed: Aug. 4, 1980

[51] Int. Cl.³ .................. G01N 27/46; G01N 33/22
[52] U.S. Cl. .................. 23/232 E; 422/94;
422/96; 422/98; 324/71 R; 73/27 R
[58] Field of Search .............. 422/94, 95, 96, 98;
23/232 R, 232 E; 73/23, 26, 27 R; 324/71 R

[56] References Cited

U.S. PATENT DOCUMENTS

| | | | |
|---|---|---|---|
| 3,791,936 | 2/1974 | Pebler et al. | 422/94 X |
| 4,128,458 | 12/1978 | Obiaya | 422/94 X |
| 4,170,455 | 10/1979 | Henrie | 23/232 E |

*Primary Examiner*—Ronald Serwin
*Attorney, Agent, or Firm*—Fitch, Even, Tabin, Flannery & Welsh

[57] ABSTRACT

Methods and apparatus for measuring combustible gases in which an active sensor is maintained at controlled, temperature in respect of a reference sensor by means of a bridge-sampling system and a variable duty cycle system responsive to the bridge sampling system adapted to periodically bypass the current from the active sensor in a reference bridge network.

10 Claims, 6 Drawing Figures

COMBUSTIBLE GAS DETECTION SYSTEM

Generally, the present invention is directed to measurement systems, and, more particularly, is directed to methods and apparatus for detection and measurement of combustible gases.

Combustible gas detectors may conventionally utilize a detector filament or catalytic detector element which may be electrically heated to provide for oxidation at the filament surface of combustible components. Such catalytic elements may be included in a detection circuit such as Wheatstone bridge circuit containing a reference element which does not provide for reaction of the combustible gas at the reference element surface. The resistance of such a catalytic element is a function of the temperature of the element, and when the filament resistance is increased by the heat of reaction of the combustible gas, the presence of the combustible gas may be detected by its differential effect on the catalytic element in respect to the reference element. However, the temperature rise of the catalytic element may be substantial, particularly in relatively high levels of combustible gas, and the temperature rise itself may further increase the reaction rate of the combustible gas at the measurement element thereby further increasing heat input to the element and providing nonlinear positive feedback to the gas detection measurement. An increase in element temperature may also place the measurement element above the threshold temperature(s) for detection of other combustible gases in a gas mixture in a relatively nonlinear, uncontrollable manner, and may adversely affect the element response, the element life, and the detection accuracy.

Various system have been proposed for maintaining measurement elements at constant temperature in varying combustible gas concentrations. However, such systems have various disadvantages, and improved systems for combustible gas detection and measurement would be desirable.

Accordingly, it is an object of the present invention to provide improved methods and apparatus for measurement and detection of combustible gases. It is a further object to provide such systems capable of providing substantially linear response to combustible gas concentration and which may be adapted for operation at constant or controllably variable detection element temperatures. These and other objects of the present invention will become apparent from the following detailed description and the accompanying drawings, of which:

Figure 1:
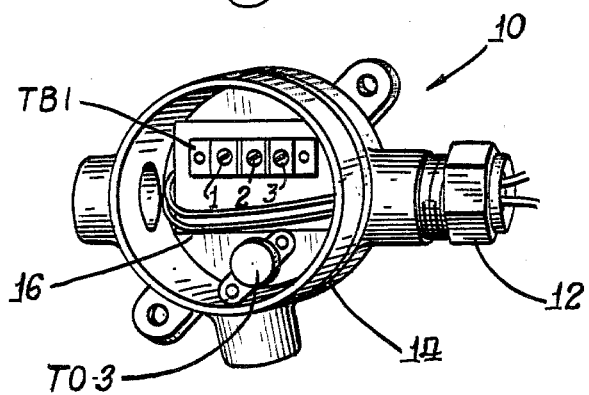
FIG. 1 is a perspective view of an embodiment of combustible gas detection measurement apparatus in accordance with the present invention.

Generally, in accordance with the present invention, methods and apparatus are provided for detection and measurement of combustible gases.

Apparatus in accordance with the invention is adapted for operation with a resistance bridge network such as a Wheatstone bridge network comprising a first current pathway comprising an active sensor resistance element which is interactive with the combustible gas to be detected, and a reference sensor resistance element. The resistance bridge network will generally further include a second current pathway comprising reference resistance elements. A further aspect of the apparatus is the provision of means for generating a control signal which should generally best be a substantially square wave signal, having a frequency which is substantially greater than the thermal response frequency (i.e., the inverse of the thermal response time of the sensor) of the active sensor resistance element. The resistance network further includes switch means responsive to the control signal for providing an alternative circuit pathway for bypassing the active sensor resistance element in the bridge network. The apparatus further comprises current source means for providing electrical current to the resistance bridge network, and means responsive to a control signal for sampling the electrical potential balance of the bridge network and for varying the duty cycle of a control signal in response to imbalance of the bridge network.

As will be discussed in more detail hereinafter, the apparatus functions in a particular manner to control and vary the resistive power input, averaged over time, which is supplied to the active sensor element as compared to that which is supplied to the reference sensor element. This control is achieved by periodically bypassing the current supplied to the active sensor resistance element, without substantially disturbing the current supplied to the reference resistance element or other appropriate elements of the resistance bridge network in order to maintaing the active-reference sensor bridge in balance, in response to non electrical power variation (such as that provided by chemical combustion) at the active sensor resistance element. In this manner, by switching on and off the current load transmitted through the active sensor, the active sensor may be kept at constant or predetermined temperature by varying the amount of electrical power fed over time to the sensor element. This resulting electrical power variation can be used to provide a direct measure of combustible gas concentration.

Further, by controlling the sensor temperature, sensor life may be increased due to minimizing of thermal stresses, non-linearities inherent in bridge imbalance measurements, and non-liner resistance versus temperature responses of sensors may be minimized, and rapid instrument response time may be provided.

Such methods can be used to measure any quantity which can cause a change in power flow from the sensor to the environment. In a catalytic type combustible gas measurement sensors, power is fed to the sensor by combustion of the gas on the surface of the sensor. In typical gas measurement systems, the sensor is placed in a Wheatstone bridge where it causes a measurable difference voltage when it heats up due to the presence of combustible gas. In a gas measurement system using a periodic power method of maintaining the active sensor resistace in fixed relationship to the reference sensor resistance, the sensor is not allowed to heat up above the predetermined operating temperature, so that electrical power must be taken away from the sensor when power is being fed to it by combustion at the sensor. Measurement reveals that this subtracted electrical power is very linearly proportional to the concentration of combustible gas at the sensor, making this period power diversion and bridge sampling technique valuable in gas measurement.

Turning now to the drawings, various aspects of the present invention will be more particularly described with respect to the embodiments there shown.

Figure 1A:
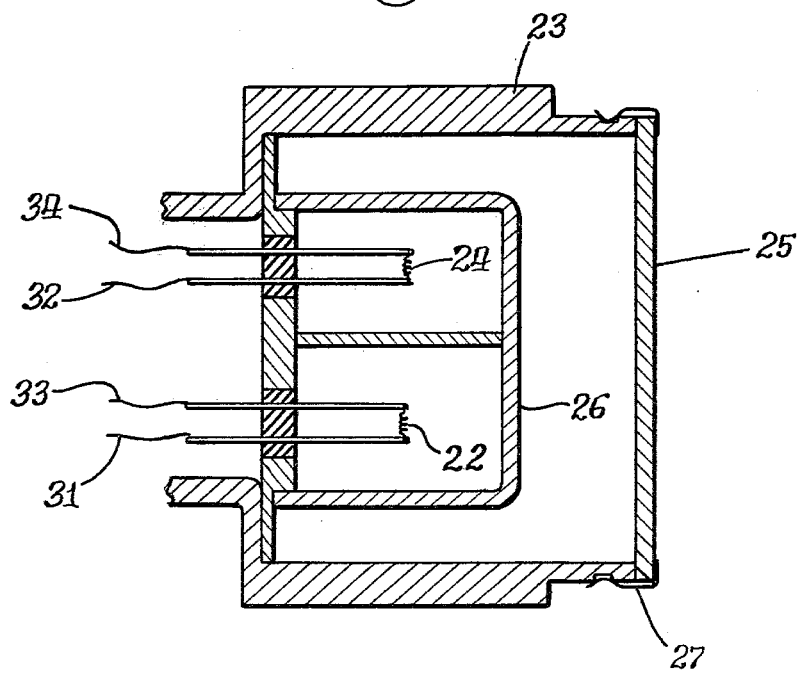
FIG. 1A is a view, partially broken away, of the active sensor and reference elements of the gas detector of the embodiment of FIG. 1.

Illustrated in FIGS. 1 and 1A is an embodiment 10 of combustible gas detection and measurement apparatus comprising a sensor module 12 and a transmitter module 14 disposed in an explosion-proof electrical housing 14 from which the cover has been removed to reveal the terminal board TB1 to which electrical connection is made to the instrument 10, and a heat-sink mounted power transistor TO-3, with the various other electronic components being located on the underside of board 16. The interior construction of the sensor module 12, which is of conventional design (e.g., manufactured by Gas Tech Corp. or Delphian Corporation of California), is shown in FIG. 1A. The module 12 comprises an active sensor resistance element 22 and a reference resistance element 24 which are isolated within an explosion-proof porous sintered stainless steel shield 26, and separated therein by a shield 28 to prevent thermal interaction between the elements 22 and 24. The illustrated active sensor element 22 and resistance element 24 each comprise a ceramic-coated fine platinum wire resistance coil which is disposed between appropriate metal leads supplied with conducting wires to the transmitter circuitry 14. However, only the active sensor 22 is provided with an appropriate catalytic coating to catalyze the oxidation of combustible gases (e.g., methane, ethane, propane, butane, carbon monoxide, etc.). In this manner, an active sensor 22 is provided which is responsive to combustible gases in the presence of oxygen, and a reference sensor substantially similar in electrical and thermal properties is provided, which is not responsive to the presence of combustible gases at operating temperatures of the device 12. The outer sensor housing 23 is similarly provided withh a porous sintered stainless steel dust cap 25 which is held in place by ring clamp 27. In operation, combustible gas may diffuse through the sintered metal cover 25 and the sintered metal cap 26 into the zone surrounding the active and reference elements 22, 24, for measurement by a sensor resistance bridge formed in part by the active sensor element 22 and the reference element 24.

The sensor bridge is utilized to maintain equal resistance of the active sensor 22 with respect to the reference sensor 24 in a particular manner utilizing a switch across the current path of the active sensor 22 to bypass the sensor 22 in the bridge, as will be explained in more detail. The bridge is only sampled when the switch across the active sensor is open, so that current is then being conducted through the sensor 22 in the normal manner.

A difference signal from the bridge is amplified and converted to a rectangular wave of varying duty cycle which can result in the provision of different amounts of electrical power to the active sensor 22 without disturbing the bridge measurement.

Normally, the sensors 22, 24 operate at substantially the same temperature when there is no combustible gas present. When combustible gas is present, the active sensor 22 would tend to become hotter. This, however, will cause an error signal, for as the sensor 22 becomes hotter, its resistance will increase. The error signal causes the active sensor 22 to be driven with a lighter duty cycle, which reduces the amount of electrical energy fed to the active sensor 22. This change in electrical energy is, over time, substantially the amount of chemical energy flowing into the active sensor, since the sensors are maintained by the apparatus 10 at substantially equal temperatures and therefore must have substantially the same amount of thermal energy delivered to each, whether all electrical or chemical and electrical in origin.

It has been shown that a gas sensor of this type held at substantially constant temperature uses a substantially linearly decreasing amount of electrical energy to keep it at one temperature in the presence of linearly increasing amounts of combustible gas. Thus the electrical duty cycle in embodying the present invention represents a linear signal proportional to gas concentration.

Figure 2:
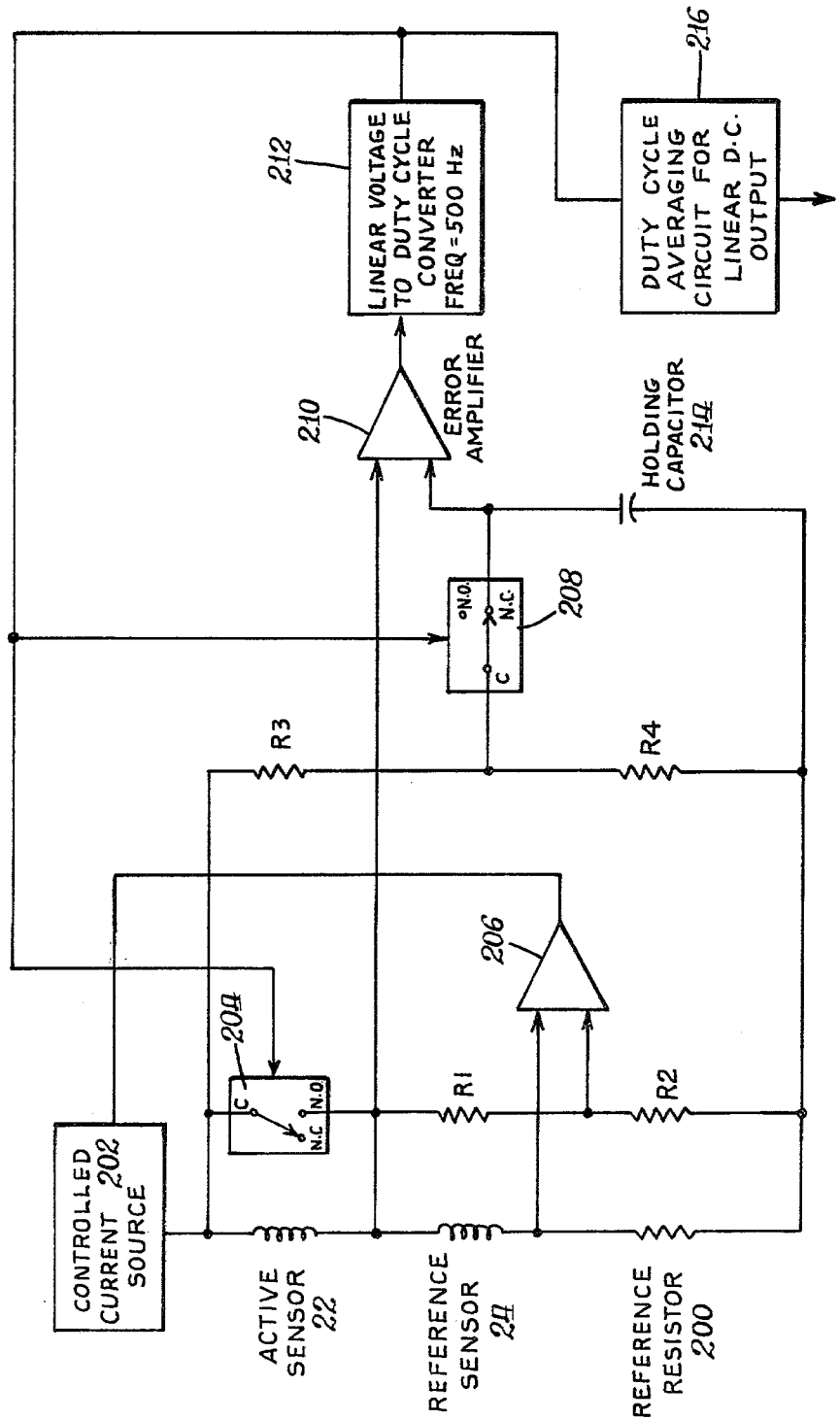
FIG. 2 is a schematic block diagram representing various of the circuit elements of the embodiment of FIG. 1, having active and reference sensors maintained at constant temperature with respect to each other and with respect to a fixed resistor.

The circuitry of the transmitter 14 utilized with the sensor element 12 is shown in schematic block diagram in FIG. 2. As illustrated in FIG. 2, the transmitter 14 comprises a controlled current source 202, a voltage to duty cycle converter 212 for providing a square wave control signal of variable duty cycle, and a bypass switch 204 for bypassing the active sensor 22 in response to the control signal from converter 212. Two wheatstone resistance bridges, the first including the reference 24 and the second including the active sensor 22 and the reference sensor 24 are used and each bridge is provided with a feedback control loop to balance the bridge under all operational conditions. The first bridge including reference resistors R1 and R2 uses differential error amplifier 206 disposed across the bridge to control the current source 202, and to control the current through the active and reference sensors 22, 24 such that the resistance of the reference sensors 24 is in a fixed relationship with that of a temperature invariant reference resistor 200. The ratio of the resistance of resistors R1 and R1 forming the other current path of the first bridge (R1:R2) will equal the ratio of the reference sensor resistance to the reference resistance. Self-heating of the reference sensor 24 increases its resistance as the current through it increases.

The second bridge comprising the active sensor 22, the reference sensor 24 and the reference resistor 200 in one path, and resistors R3 and R4 in another path, uses differential amplifier 210 and converter 212 to control the amount of energy fed to the active sensor 22. Converter 212 opens and closes switch 204 at a frequency of 500 HZ, which is substantially greater than the thermal response frequency of the sensor 22, on a duty cycle determined by the output voltage from the differential amplifier 210 which is adapted to respond to voltage differences across the second bridge. When the active sensor 22 needs more electrical energy, switch 204 is left open a greater percentage of the time so that the current from current source 202 will flow through the active sensor 22 more of the time and thus heat it up. Since the secnd bridge comprising resistors R3, R4 the reference resistor and the sensors 22, 24 cannot be a bridge when the active sensor 22 is shunted by switch 204, switch 208 is used in conjunction with capacitor C1 to form a sample and hold circuit which yields a DC signal to error amplifier 210. Resistors R1 and R2, while not principal components in this second bridge, do enter into play. When set so that a small fraction (e.g., 5–20%) of the reference sensor current flows through them, the active sensor 22, when not shunted, will receive additional current over that flowing in the reference sensor 24. This will cause the error amplifier 210 to run the active sensor 22 at duty cycle of less than 100 percent for equal temperatures in a sensor pair with well matched resistances at the desired operating temperature. Nominal manufacturing tolerances can thus be accommodated by the duty cycle loop without saturation. For example, if about 5 percent of the reference sensor current flows through resistors R1 and R2, the active sensor 22 will receive about 5 percent more current (when not shunted) than the reference sensor 24, which will cause the error amplifier 210, by means of the converter 212 and switch 204, to conduct current through the active sensor 22 at a duty cycle of about 90 percent. This means that 90 percent of the time period of each cycle of the control signal from converter 212 (and hence, 90 percent of the time on average), the current from source 202 is conducted through active sensor 22, and 10 percent of the time of each cycle it is conducted through switch 204.

Because the electrical power provided to the active sensor 22 is directly proportional to the duty cycle, the chemical power due to gas combustion at the active sensor 22 can be determined by noting the change in duty cycle when combustible gas is present. Duty cycle averaging circuit 216 provides a linear DC output signal representing the average of the duty cycle signals from circuit 212. A linear frequency output could also be obtained by using a voltage to frequency converter with output pulses of constant length. As such, it could replace the fixed frequency voltage to duty cycle converter 212. The output frequency of such a circuit system would be proportional to the duty cycle and thus provide a linear pulse frequency output representative of combustible gas concentration.

The illustrated periodic power diversion circuitry provides a high degree of accuracy to the catalytic method of combustible gas measurement. In this regard, it is known that different gases may commence catalytic activity at different temperatures. However, if the voltage is swept across the reference and active sensors in a conventional bridge in the presence of different gases, the thermal input provided by combustion causes difficulties in respect of analysis of the different thresholds. Because in a conventional constant voltage reference sensor bridge, for each time the threshold temperature of a gas is reached, the temperature increases, which in turn increases catalysis to increase temperatue, etc. This positive feedback situation accordingly produces a response curve in the presence of mixed combustible gases which is difficult to analyze. However, apparatus in accordance with the present invention may be provided in which the reference and active sensors are controllably swept through a desired temperature range to produce a response curve which may be analyzed for multiple gases having different threshold catalysis or detection temperatures.

Furthermore, two active sensors may be provided in one or more bridges which have slightly offset voltage versus temperature characteristics. For example, one active sensor may be provided which is operated at a temperature which is maintained at a fixed temperature differential (e.g., a temperature in the range of 25°–100° F. from the temperature of another active sensor. A response signal will appear for each gas only when the two sensors are in the region where one sensor reacts to the particular gas and the other does not. Effectively dual active sensor systems may be provided by analyzing the response curve of a single sensor swept through a temperature range, by subtracting values obtained at a time differential, provided the gas composition does not substantially change during the measurement period.

Figure 3:
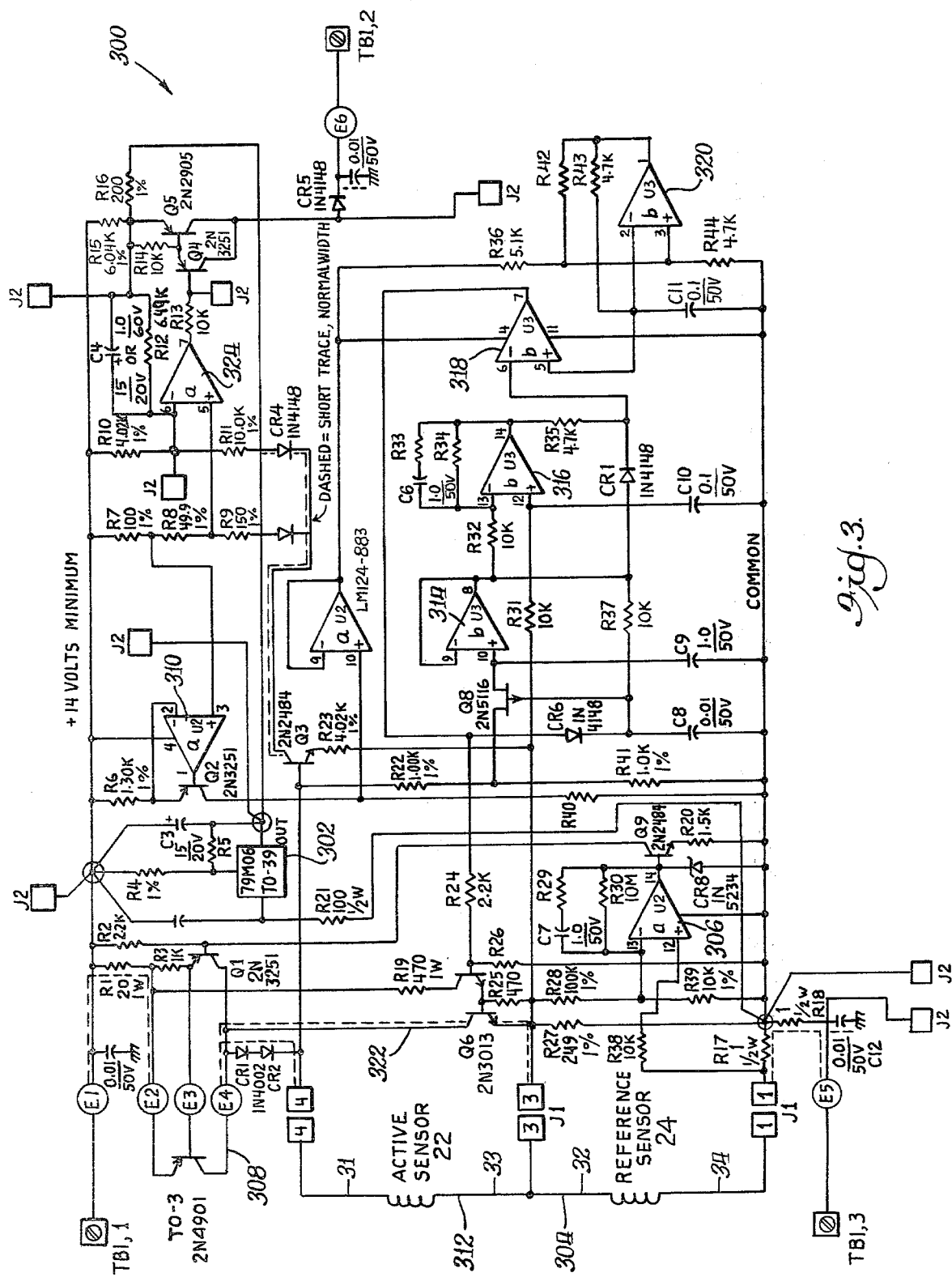
FIG. 3 is a circuit diagram of the embodiment of FIG. 1 illustrating the circuit components thereof and the manner of their interconnection.

Illustrated in FIG. 3 is the circuit embodiment 300 of the transmitter 12 shown in block diagram form in FIG. 2. The circuit 300 of FIG. 3 comprises voltage reference circuit 302, bias voltage circuit 310 and a reference temperature control feedback loop comprising feedback balanced bridge circuit 304, error amplifier circuit 306, and controlled current source circuit 308. The circuit 300 further includes a sensor control and gas measurement feedback loop comprising feedback balanced bridge circuit 312, sample and hold circuit 314, error amplifier circuit 316, comparator circuit 318, floppy triangle wave oscillator 320, active sensor bypass switch circuit 322 and duty cycle to DC converter circuit 324.

Generally, the circuit components are shown on FIG. 3 with commercially available component part designators. Resistance values are in ohms (1% resistors RN 55C, others ¼ watt 5% unless otherwise specified). Capacitor values are shown in microfarads, and short, thick printed circuit board lines are shown by dashed line enhancement. Plug terminal connectors are shown as identically numbered blocks, while wire connectors to the circuit board as shown in circled E designators.

The voltage reference circuit 302 provides reference voltage primarily for the duty cycle to DC converter circuit 324 although it also provides reference voltage for a bias circuit 310. The voltage reference circuit 302 comprises voltage regulator U1, resistors R21, R4 and R5, and capacitors C2 and C3, configuration of which will depend on the actual type of device used for the voltage regulator U1. The illustrated circuit 300 uses a negative six volt, 3 terminal voltage regulator, designated 79 MO6, as manufactured by Fairchild, Motorola and National Semiconductor, and for this device, resistor R4 is replaced by a short circuit and R5 is replaced by an open circuit.

In operation, the device 10 is provided with a power supply of at least +14 volts to terminal TB1, 1, which may be externally supplied through conduit connectors as shown in FIG. 1. The ground, common line, is similarly externally connected to terminal TB1, 3. The voltage regulator U1 functions to provide at its output terminal a line 6 volts below the plus 14 volt line (at the top of the schematic) for utilization by various components of the circuit 300 of FIG. 3.

As previously generally described in respect of FIG. 2, a feedback loop including a first Wheatstone bridge is provided to maintain the reference sensor at substantially constant temperature and comprises the feedback bridge 304, the error amplifier 306, and the controlled current source 308. The reference sensor temperature compensation bridge 304, which is to be balanced by feedback, comprises reference resistance elements R17, R28 and R39, in addition to the reference sensor 24. The reference resistance elements may vary in resistance according to the temperature at which it is desired to operate the reference element 24 of the instrument 10.

As more current goes through the reference element, its resistance will increase in view of the positive temperature coefficient of its resistance. Current is adjusted through the bridge 304 to establish the balance point of the bridge by the feedback control system, which maintains this balance in operation regardless of the ambient temperature. In the bridge 304 this balance is achieved when the ratio of the temperature dependent resistance of the reference sensor 24 to the resistance of resistor R17 will equal the ratio of R28 to R39, which in the illustrated embodiment occurs when the reference sensor 24 has a resistance of 10 ohms (at desired operating temperature).

One element of the feedback components which balance bridge 304 is the error amplifier 306. The error amplifier 306 is connected to the respective center points on each leg of the bridge 304 and functions to keep the voltages equal at the bridge center points by varying the current to the reference sensor to change its resistance. Accordingly, the error amplifier 306 functions to change the voltage occurring between the reference sensor 24 and resistor R17 and be able to match it up with the voltage occurring between R28 and R39. Included in the error amplifier feedback circuit 306 are resistors R38, R29, R30, capacitor C7 and differential amplifier U2 pins 12, 13 and 14. The illustrated embodiment 300 is provided, over all, with eight differential amplifier circuits, which are integrated in groups of four on two LM124 integrated circuit devices (designated "U2" or "U3" in FIG. 3) of the type sold by National Semiconductor and a number of other companies. The individual differential amplifier circuits are designated by device and pin designations in accordance with practice in the art. Differential amplifier U2, pins 12, 13, 14 functions to maintain pins 12 and 13 at the same voltage. Resistors R38 and R30 together set the gain of the error amplifier U2, pins, 12, 13, 14. Capacitor C7 and resistor R29 are feedback loop compensation components used to obtain stability of the loop.

Another component of the feedback loop is the controlled current source 308 which comprises diode CR8, transistors Q9, Q1, resistors R2, R3, R1 and R20 and a 2N4901 power transistor in a TO-3 package. The error amplifier 306 output is provided to the base of transistor Q9 creating a current output through the collector of transistor Q9, which is controlled by the value of resistor R20 and the voltage at the base of transistor Q9. This current is limited by diode CR8 so that as the error amplifier 306 searches for its proper value, it will not burn out the sensor 24 by putting too much current through it. That control current coming out of the collector of transistor Q9 causes a voltage to appear across resistor R2. The voltage is transferred also into the base of transistor Q1 and through the emitter of transistor Q1 through the base and the emitter of the TO-3 transistor which creates a voltage across resistor R1. This voltage produced across resistor R1 is changed into a current which flows through the collector of the TO-3 transistor through either the active sensor 22 and the diodes CR1 and CR2, or through the active sensor bypass switch 322 formed by transistor Q6 (which will be described in more detail hereinafter), down into the reference sensor bridge. Components CR1, CR2 and Q6 (not part of the reference sensor bridge 304) represent two alternate paths by which the current may travel from the current source output at the collector of the TO-3 transistor down into the bridge.

Having described the reference temperature control circuitry, other aspects of the circuitry of the instrument 10 shown in FIG. 3 will now be described. In this regard, a bias voltage circuit 310 is provided in addition to the voltage reference circuit 302, for providing a bias voltage for the U3 operational amplifiers. The bias voltage circuit 310 utilizes the relative negative 6 volts reference output of voltage reference circuit 302, and creates a 12 volt bias voltage as shown in FIG. 3. In the circuit 310, two of the four operational amplifiers of the U2 device are used. Device U2, pins 1, 2 and 3, and U2, pins 8, 9 and 10, in addition to transistor Q2, and resistors R7, R8, R9, and R40. The bias voltage circuit 310 divides the negative 6 volts reference down to a negative 2 volts which occurs between resistor R7 and R8. The negative 2 volts is fed into the noninverting input of U2, pins 1, 2 and 3 and thus that negative 2 volts is transferred to the inverting input and also to resistor R6. The current through resistor R6 cannot go into the inverting input in the amplifier so it must flow through transistor Q2. Most of the current goes directly through transistor Q2 to the collector into resistor R40 where approximately 12 volts bias voltage is created, which is in turn fed into the noninverting input of differential amplifier U2, pins 8, 9 and 10. Device U2, pins 8, 9, 10 is connected as a voltage follower so that a low impedance 12 volt bias voltage occurs at pin 8 of device U2. The 12 volt bias voltage is provided to the circuits of integrated circuit device U3, as shown in FIG. 3.

The feedback circuitry for maintaining the reference sensor 24 at a desired temperature has previously been described. A second Wheatstone bridge and associated control circuitry, which will now be described in detail, is of particular importance to the instrument 10, and functions to keep the active sensor 22 at the same resistance as the reference sensor 24. The control system functions by varying the electrical power delivered to the active sensor 22 by periodically shunting the power around the active sensor 22 in its bridge circuit, without periodically bypassing the reference sensor component of its bridge. Accordingly, when the active sensor 22 is provided with combustion energy by the presence of a combustible gas, the circuitry is adapted to reduce the amount of electrical power fed to the active sensor 22 so that it may stay at constant temperature and thus constant resistance. The components of this active sensor control feedback loop comprise the bridge 312 which is to be balanced by feedback, sample and hold circuit 314, error amplifier 316, comparator 318, floppy triangle oscillator 320, active sensor bypass switch 322, and duty cycle to DC converter 324.

The active sensor bridge 312 to be balanced by feedback comprises the active sensor 22, the reference sensor 24 and the reference resistor R17 in one resistance leg. A third resistance parallel with the reference sensor 24 and the reference resistor R17, represented by resistor R27 is provided to accommodate manufacturing tolerances, etc. in the active and reference sensor unit 12. In this regard, the resistor R27 is provided parallel to the reference sensor so that when the first bridge 304 is balanced, the reference sensor 24 will have the proper current to keep it at the proper temperature, but the current that must flow through the active sensor 22 from the current source 308 will be about 10% greater (except when shunted) than that passing through the reference sensor 24 because a portion of this current is conducted through resistor R27. Thus, in a system where the two sensors 22, 24 have exactly the same temperature versus resistance characteristics, the active sensor 22 will have to be maintained at a duty cycle of 70 to 80% (rather than 100%) to provide balance of the bridge 312, as will be explained in more detail hereinafter. When the sensors 22, 24 don't match exactly, duty cycle variance may be utilized to accommodate such differences. The other leg of the active sensor control bridge 312 is provided by resistors R22 and R41, as shown in FIG. 3.

Because current is not continuously provided to the active sensor 22 in the bridge 312, the bridge 312 may not be tested for a balanced condition in the conventional continuous manner, and a sample and hold circuit 314 is provided to periodically sample the bridge 312 only when the active sensor is being provided with current. The sample and hold circuit 314 for the bridge 312 is provided to sample the bridge at a particular point in the discontinuous feedback cycle. More specifically, because the active sensor 22 is being switched on and off all the time, it does not continuously have appropriate bridge voltage, and to provide an accurate bridge measurement, the signal from the bridge 312 must be sampled only when there is in fact current going through the active sensor 22. The illustrated sample and hold circuit 314 is particularly adapted to provide the necessary periodic sampling of the active sensor bridge, and comprises transistor Q8, differential amplifier U3, pins 8, 9 and 10, resistor R37, diode CR6, and capacitors C8 and C9. The sample and hold circuit 314 is switched on and off by means of transistor Q8. The gate of transistor Q8 is turned on by the control input at the anode of diode CR6. A square wave control signal (as subsequently described) is applied to that input (and to the switch 322) which functions to turn on and off at the sample and hold circuit 314. When the square wave signal rises, the current from the square wave source 318 flows through diode CR6 into the gate of transistor Q8, and also to resistor R37 and capacitor C8. The role of resistor R37 and capacitor C8 is to provide a fast "turn-off", but a slow "turn-on" of the sample and hold gate. In this regard, when the square wave control signal input rises, this rise causes transistor Q8 to turn-off very rapidly, because the square wave source driving the sample and hold circuit is a low impedance source which fills capacitor C8 with charge very easily. However, when the square wave input falls to turn on transistor Q8, then diode CR6 blocks the square wave input and even though the square wave input goes down very quickly, capacitor C8 will remain high and be discharged slowly through R37. This creates a delay such that transistor Q8 turns on relatively slowly. This provides the appropriate timing in the circuit for proper sampling operation at the indicated control signal frequency. The hold capacitor is capacitor C9. Whenever transistor Q8 is closed to tap off the bridge voltage, then capacitor C9 charges up until it reaches that same bridge voltage. Then when transistor Q8 is opened, capacitor C9 holds that voltage until the next sampling cycle. Capacitor C9 is chosen to have such a value that even with the leakage current of transistor Q8 and differential amplifier U3, pin 10, it will hold the voltage for long enough to provide stability in the circuit. The output of the sample and hold circuit 314 is provided at differential amplifier U3 pin 8 to an error amplifier circuit 316. The error amplifier 316 is accordingly effectively connected to both legs of the bridge by the sample and hold circuit 314, the one leg leading from the resistors R22 and R41 having been sampled at appropriate times by the sample and hold circuit 314, and the other leg being connected through resistor R31 directly to the center of the bridge 312 containing the active and reference sensors. Because the center of the bridge 312 is maintained at substantially constant voltage with respect to the square wave control signal frequency, no periodic sampling in respect thereto is necessary.

The error amplifier 316 comprises resistors R31, R32, R33, R34, R35, capacitors C6 and C10, diode CR7 and differential amplifier U3, pins 12, 13 and 14. Capacitor C10 functions to reduce noise at the noninverting input of differential amplifier U3, pins 12, 13 and 14. Resistors R32 and R34 determine the gain of the error amplifier U3, pins 12, 13 and 14. Capacitor C6 and resistor R33 are feedback loop compensation components which function to provide stability of the circuit feeback loop. Resistor R35 and diode CR7 form a clamp which limits the output voltage of the error amplifier 316 to a predetermined voltage so that it is not possible to go to a duty cycle of 0%, where the active sensor is always off. In such circumstances, the sample and hold circuit 314 would never sample, because it only samples during the time when the active sensor 22 is provided with current. Accordingly, clamp components R35 and CR7 are added to limit the duty cycle to prevent the active sensor from being completely turned off. The output of the error amplifier 316 provided at the clamp at the junction of resistor R35 and diode CR7, is fed into the comparator circuit 318 which generates the square wave control signal used to control the active sensor bypass switch 322 and the sample and hold circuit 314. The comparator circuit 318 also receives input from floppy triangle wave oscillator 320. The output from the floppy triangle wave oscillator 320 is used by the comparator 318 to vary the duty cycle of this control signal to the bypass switch 322 and sample and hold circuit 314. The floppy triangle wave oscillator 320 comprises resistors R36, R44, R43 and R42, capacitor C11 and differential amplifier U3, pins 1, 2 and 3. In operation, the oscillator 320 produces a wave shape at pin 2 of differential amplifier which is roughly like a triangle wave, except that it is slightly curved (hence the designation "floppy"). The output of the error amplifier 316 from the clamp of resistor R35 and diode CR7 is compared with this triangle wave by the comparator 318. As the DC voltage output from the error amplifier 316 is changed, then a square wave output from the comparator 318 is provided which is of variable duty cycle. In this regard, sampling at the "top" of the triangle wave output of the triangle wave oscillator 320 provides a very narrow square wave output from the comparator 318, while sampling at the middle of the triangle wave provides a square wave output from the comparator 318 of approximately 50% duty cycle, and sampling at the base of the triangle wave provides a square wave output of relatively large duty cycle. Accordingly, as the duty voltage changes, the output of the error amplifier is compared with the triangular wave to produce a variable duty cycle output. The variable duty cycle output is the circuit feedback signal which functions to control the temperature of the active sensor 22.

The comparator 318 comprises differential amplifier U3, pins 5, 6 and 7. The output of the comparator 318 is a square wave which is fed back to the sample and hold circuit 314 as previously described, and which is also fed to the active sensor bypass switch 322.

The active sensor bypass switch is an important component of the feedback control loop for the active sensor of instrument 10. The active sensor bypass switch 322 comprises resistors R19, R24, R25, R26, diodes CR1 and CR2 and transistors Q6 and Q7. The purpose of resistors R24 and R26 is to form a threshold voltage so that the switch 322 will not turn on until sufficient voltage has been created at the input to the sample and hold circuit 314 such that the sample and hold circuit 314 has turned off. In this manner, it is assured that the sample and hold circuit 314 is turned off before the active sensor 22 is shorted. Then once transistor Q7 and Q6 turn on, the active sensor 22 is shorted (i.e., current is bypassed around the sensor 22). Diodes CR1 and CR2 are placed in series with the active sensor 22 (although not in any bridges) to insure that the active sensor 22 actually receives zero volts and zero current when the switch 322 is on. Transistor Q6 has a saturating voltage which is non-zero such that if only transistor Q6 were used to short the active sensor 22 then a small amount of current could still flow through the sensor. Hence, by shorting out the combination of the active sensor 22 and diodes CR1 and CR2 in series, it is guaranteed that negligible current will flow through the active sensor 22 when the switch 322 is shorted. As previously indicated, balancing of the active sensor feedback loop requires that the active sensor 22 be at the same resistance as the reference sensor 24 plus the reference resistor R27, which is also accounted for in the value of the resistors R22 and R41 of the other leg of this bridge 312. Once a loop is established, then there will always be a certain duty cycle of current occuring across the active sensor 22 to keep the bridge 312 in balance. When combustible gas is introduced to the active sensor 22, it will be provided with additional thermal input which would tend to unbalance the bridge 312 and hence causes the duty cycle of current directed through active sensor to decrease in the total amount of electrical power fed to it (over time) to keep the bridge 312 in balance. The measurement utilization of this duty cycle change to achieve bridge balance in the illustrated embodiment 300 involves conversion of the duty cycle information to a DC quantity by the duty cycle to DC converter 324.

The illustrated duty cycle to DC converter circuit comprises resistors R23, R9, R8, R7, R11, R10, R13, R12, R14, R15, R16, diodes CR3 and CR5, transistors Q3, Q4, Q5, differential amplifier U2 pins 5, 6 and 7 and capacitor C4. The duty cycle to DC converter 324 functions in response to the duty cycle of the control signal for turning on and off of the active sensor 22. As the active sensor 22 goes on and off, transistor Q3 is turned on and off. When transistor Q3 is on, a current is provided which flows through resistor R23 to the collector of transistor Q3 and to the diodes CR3 and CR4. The amount of current flowing through diode CR4 is adjusted so that the current flowing in diode CR3, which remains, will be approximately similar to that in CR3, making the voltage drop across diodes CR3 and CR4 substantially equal and making the voltage occuring at the junction between diode CR4 and resistor R11 substantially equal to the minus 6 volts of the voltage reference, whenever transistor Q3 is on. When transistor Q3 is off, then no current will flow through resistor R11. Resistors R7, R8 and R9 form a reference divider which provides a three volt potential directed to the noninverting input of differential amplifier U2, pins 5, 6 and 7. At the inverting input of the differential amplifier, which is a current summing node, there is a constant current which is created by this three volt potential flowing through R10 and a variable current created by the variable duty cycle (on-off) of the three volt potential provided across resistor R11. This variable current and the fixed current are combined at the current summing node and occur as a voltage at the emitter of transistor Q5. This resultant voltage is provided as a DC voltage because of capacitor C4, which has an averaging or integrating effect on the variable duty cycle at the input. Resistor R13, transistors Q4 and Q5, and resistors R14, R15 and R16 form a current source, the current of which is determined by the voltage at the emitter of transistor Q5. In normal operation of the illustrated embodiment, the emitter of transistor Q5 is designed to vary between minus 6 volts and minus 10 volts. Under such circumstances, from approximately 1 to 20 milliamperes will flow out of the collectors of transistors Q4 and Q5. This direct current then flows out through diode CR5 to provide a measure of combustible gas concentration. R16 is the main resistor by which the voltage at the transistor Q5 emitter is turned into a current. Resistor R15 provides an idle current for which the voltage at the Q5 emitter is exactly six volts, then an idle current of 1 milliampere will still flow through Q5 and out to TB1, terminal 2 as an output signal of the instrument 10.

Also provided in the circuitry 300 is a current measuring resistor R18 intended for measurement of the current flowing in the transmitter 300, and capacitors C1, C5 and C12 which are for suppression of noise that could otherwise come into the transmitter 300. Further incuded are transmitter terminal connections indicated by terminal J2 for remote monitoring or calibration of the instrument 10.

In operation, the instrument 10 may be activated and permitted to come to thermal equilibrium under conditions in which no combustible gas is present at the detector 12. The output signal at TB1, 2 may then be registered, or "zeroed", as the zero concentration response signal. A known concentration of a selected combustible gas may then be introduced to the detector 12, and upon stabilization, the change in the output signal from the circuit 324 provided at TB1, represents the instrument response to this known gas concentration, so that the instrument 10 may thereupon be calibrated. For reasons previously discussed, the response of the instrument 10 is substantially linear with respect with the concentration of a given combustible gas at the detector 12.

As indicated previously, different combustible gases may have, for a given detection or catalyst system, different combustion temperature thresholds which may be detected by sweeping one or more active sensors over a predetermined temperature range.

In the circuit embodiments of FIG. 3, however, sweeping the voltage across the reference sensor 24 (e.g., by varying the resistance ratio between resistors R28 and R29 to vary the temperature of reference sensor 24 would also change the ratio of the reference sensor 24 to its parallel resistor R27, this in turn produces a commensurate change in the duty cycle on the active sensor 22 and produces zero gas signal dependence on reference sensor voltage, which would require compensation of the output data.

Figure 4:
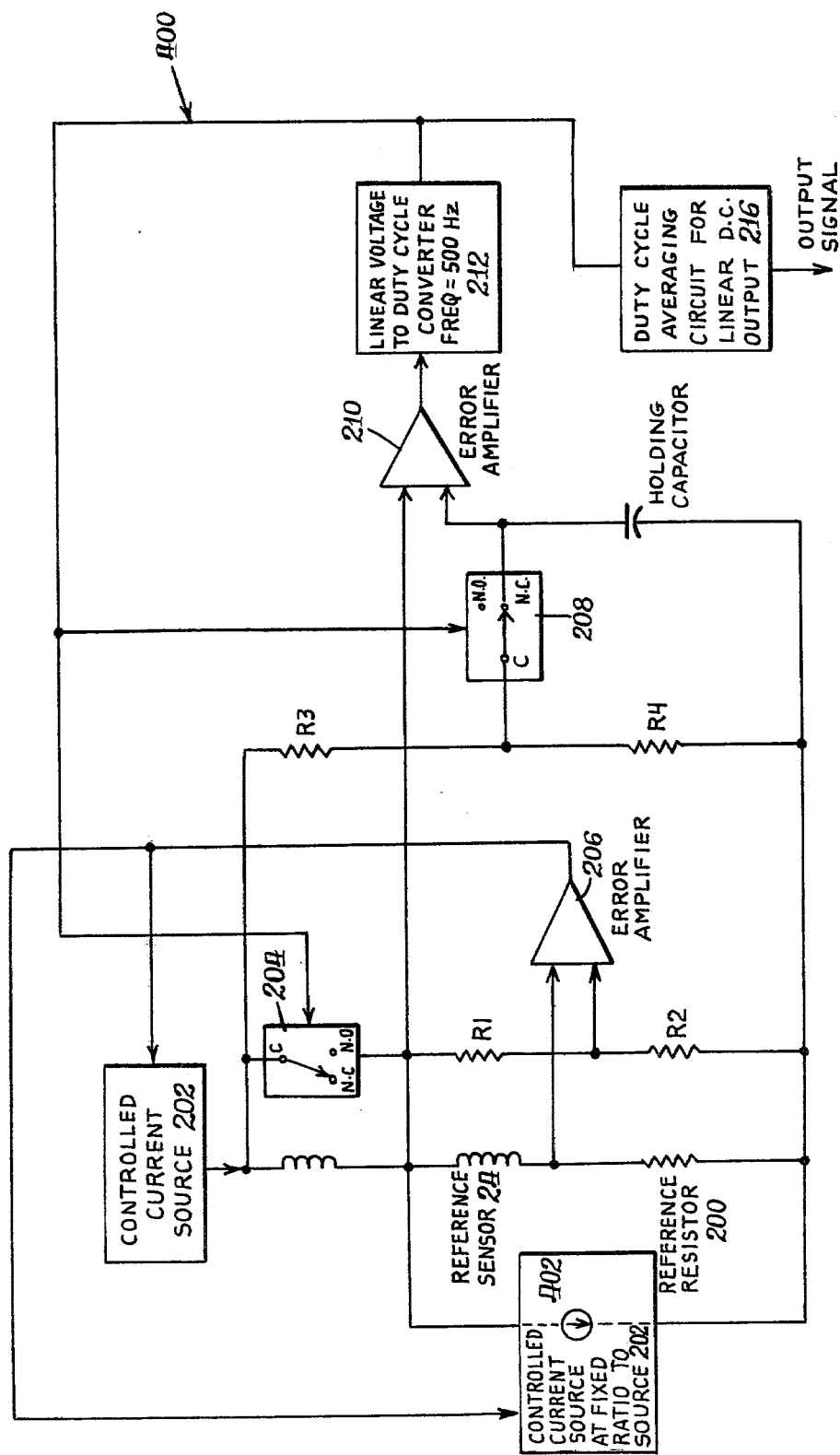
FIG. 4 is a schematic block diagram of apparatus like that of FIG. 2, which has been modified to provide for controllably variable temperature measurement for applications such as detection and measurement of mixtures of combustible gases.

Illustrated in FIG. 4, is an embodiment 400 which is particularly adapted for temperature variation of the reference and active sensors. The parallel resistor R27 is replaced by a controlled current source 402 which provides a current at a fixed current ratio (e.g., one tenth of the current output of the 202 source) to the current provided by controlled current source 202 (source 308 of FIG. 3). The resistance of the other leg of the bridge, R1 and R2 (R28 and R39 of FIG. 3) should be very high so as to function only as a voltage leg of the bridge with negligible current drain. When the resistance of the reference sensor 24 changes, the ratio of currents flowing through the two sensors 22, 24 (when the active sensor 22 is receiving current) remains constant. The modified circuit of FIG. 4 does not have a zero gas signal dependence on reference sensor resistance, and is accordingly particularly adapted for temperature sweeping analysis.

The swept-temperature system 400 may be operated in two ways: (1) by sweeping either resistor R1 or R2 (R28 and R39 of FIG. 3) using a variable resistor, or (2) by not using the reference sensor feedback bridge and operating the (ganged) current sources directly (in applications where absolute temperature is not crucial or where it is regulated as in a laboratory situation). In this second situation, the use of a reference gas could provide a marker. The second method has the further advantage of requiring only one feedback loop to stabilize during sweeping.

Figure 5:
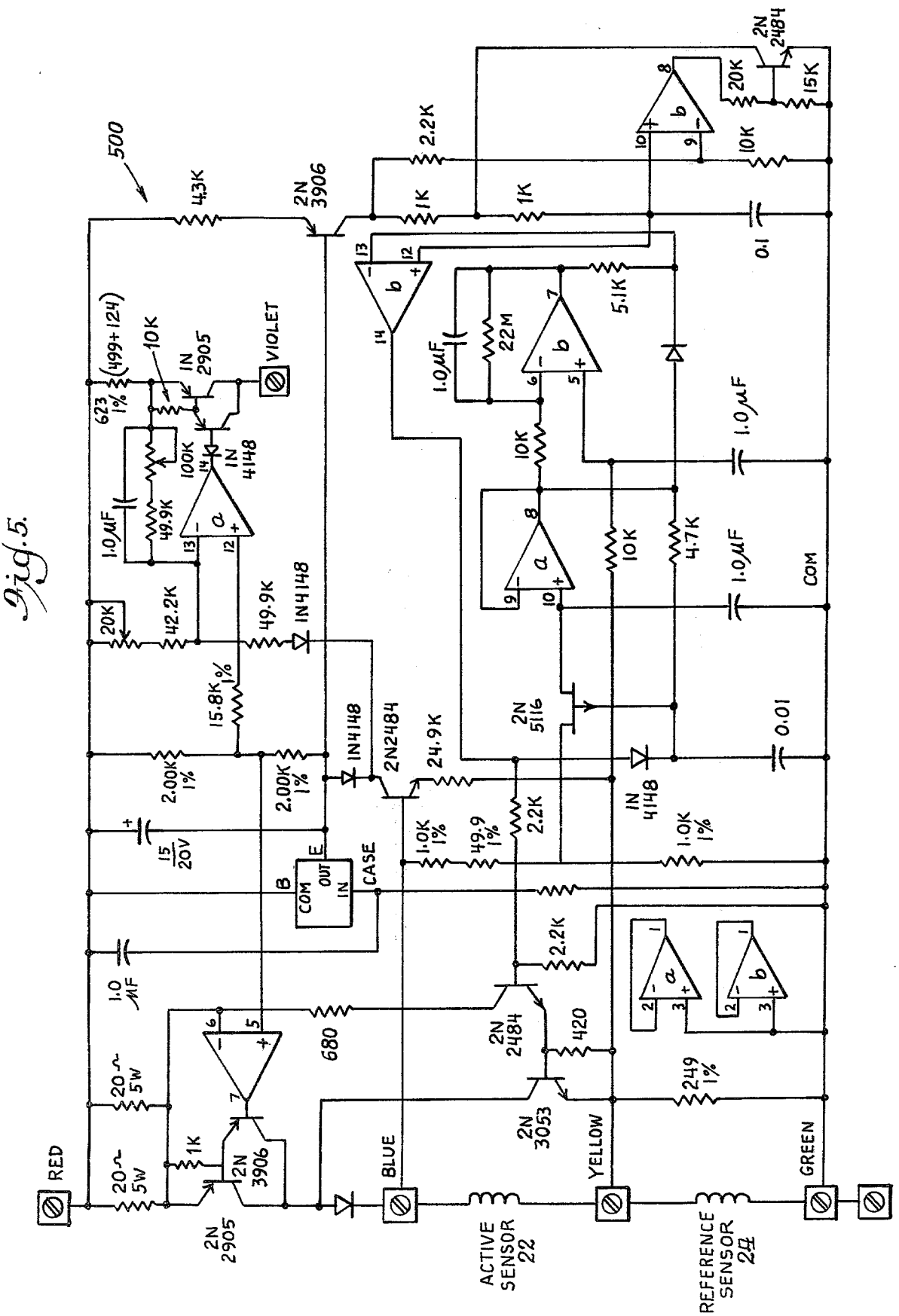
FIG. 5 is a schematic diagram of an embodiment of combustible gas detection apparatus which is not provided with temperature compensation.

In this latter connection, illustrated in FIG. 5 is a circuit diagram of a simpler embodiment 500 of gas detection apparatus which is not temperature compensated. In the circuit 500, the temperature of the sensor 22 is not kept absolutely constant but is instead matched to that of the reference sensor 24 (which is substantially similar to the catalytically active sensor in every way except that it has no catalyst on its surface). The reference sensor 24 is then operated at a constant voltage or current. Being similar to the active sensor, it allows the system to discern how much electrical power flows out of the reference sensor versus what power flows out of the active sensor. If the two powers are equal, then there is no gas present. If less electrical power being fed to the active sensor than to the reference sensor in order to maintain equal temperatures, then the difference power is due to chemical power being produced on the surface of the active sensor. However, this system 500 will be more or less sensitive to gas as the ambient temperature changes, because the reference sensor is not temperature controlled. In as much as the catalytic reaction is temperature dependent, so is the signal obtained from it. Temperature compensated systems are preferred.

In view of the present disclosure, it will be appreciated that effective combustible gas detection and measurement methods and apparatus have been provided. Various modifications will become apparent based on the present disclosure, and are intended to be within the spirit and scope of the present invention.

Various features of the invention are set forth in the following claims.

What is claimed is:

1. In a method for detecting combustible gas comprising the steps of placing active sensor and reference sensor elements of a resistance bridge in contact with a gas sample to be analyzed, and providing an electrical current across the bridge, the improvement comprising the steps of periodically diverting the current from the active sensor in response to a feedback control signal without periodically diverting said current from said reference sensor,
periodically sampling the balance of the resistance bridge while current is flowing in said active sensor to provide a bridge balance signal
controlling in response to said bridge balance signal, the average time percentage of current diversion from said active sensor to maintain balance of the resistance bridge, and
utilizing the average time percentage of current diversion from said active sensor to provide a measure of the concentration of combustible gas at the active sensor.

2. A method in accordance with claim 1 comprising the further step of adjusting the current through the reference sensor to maintain the reference sensor at a predetermined temperature.

3. A method in accordance with claim 1 wherein said current is diverted from said active sensor at a duty cycle in the range of from about 10 percent to about 90 percent and at a frequency of at least about 250 hz.

4. A method in accordance with claim 1 comprising the further step of slowly, with respect to the frequency of current diversion, varying the current through the reference sensor to vary the operating temperature of the reference and active sensors to analyze for the presence of combustible gases having different detection temperature thresholds.

5. A method in accordance with claim 1 in which two active sensors are swept over a predetermined temperature range while maintaining a temperature differential between the two active sensors and in which the differential between the average time of current diversion of the two active sensors is utilized as a measure of the presence of one or more combustible gases.

6. A combustible gas detection instrument comprising
a resistance bridge comprising an active combustible gas detection sensor and a reference sensor in one current path thereof,
means for providing an electrical current through said resistance bridge,
switch means for periodically shunting all current in said bridge from said active sensor in response to a control signal without shunting current from said reference sensor,
bridge sampling means for periodically sampling the balance of said resistance bridge when electrical current is being conducted through said active sensor and for providing an output signal representative of bridge imbalance,
means responsive to said bridge sampling means output signal for generating a variable, periodic control signal for said switch means for maintaining the resistance of said active sensor and the resistance of said reference sensor in fixed relationship by varying the average percentage of time that electrical current is conducted through said active sensor, whereby said periodic control signal provides a measure of the concentration of combustible gas at said active sensor.

7. An instrument in accordance with claim 6 further including means for preventing the simultaneous sampling of said bridge by said bridge sampling means and the shunting of current by said switch means.

8. An instrument in accordance with claim 7 wherein said control signal is a periodic signal having a predetermined frequency of at least about 250 Hz and wherein said control signal generating means varies the duty cycle of said control signal in response to bridge imbalance detected by said bridge sampling means.

9. An instrument in accordance with claim 8 further including means for maintaining said reference sensor at a predetermined temperature.

10. An instrument in accordance with claim 9 wherein said bridge sampling means comprises a sample and hold circuit and an error amplifier, wherein said control signal generating means comprises a floppy triangle wave oscillator and a comparator for the floppy wave triangle oscillator output and the output of said error amplifier, and further comprises a duty cycle to DC converter for providing an output signal linearly representative of combustible gas concentration from said variable duty cycle control signal.

* * * * *